(12) United States Patent
Hillion et al.

(10) Patent No.: US 7,566,794 B2
(45) Date of Patent: Jul. 28, 2009

(54) METHOD FOR MANUFACTURING ETHYL ESTERS FROM FATTY SUBSTANCES OF NATURAL ORIGIN

(75) Inventors: Gérard Hillion, Herblay (FR); Bruno Delfort, Paris (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 137 days.

(21) Appl. No.: 11/523,735

(22) Filed: Sep. 20, 2006

(65) Prior Publication Data

US 2007/0073070 A1    Mar. 29, 2007

(30) Foreign Application Priority Data

Sep. 21, 2005    (FR)    ................................... 05 09734

(51) Int. Cl.
*C11C 3/00* (2006.01)
(52) U.S. Cl. ..................... 554/168; 554/161; 554/167
(58) Field of Classification Search ................. 554/161, 554/167, 168
See application file for complete search history.

(56) References Cited

U.S. PATENT DOCUMENTS

| | | | | |
|---|---|---|---|---|
| 4,303,590 | A | * | 12/1981 | Tanaka et al. ............... 554/167 |
| 5,354,878 | A | * | 10/1994 | Connemann et al. ........ 554/167 |
| 5,434,279 | A | | 7/1995 | Wimmer et al. |
| 5,514,820 | A | | 5/1996 | Assmann et al. |
| 2003/0004363 | A1 | | 1/2003 | Koncar et al. |

OTHER PUBLICATIONS

Schuchardt, et al., Transesterification of Vegetable Oils: a Review, 1998, vJournal of Brazilian Chemical Society, vol. 9, No. 9, pp. 199-210.*

* cited by examiner

*Primary Examiner*—Porfirio Nazario Gonzalez
*Assistant Examiner*—Yate' K Cutliff
(74) *Attorney, Agent, or Firm*—Millen, White, Zelano & Branigan, P.C.

(57) ABSTRACT

A method allowing, from natural fat or oils, or from other glyceride mixtures, to obtain fatty acid ethyl esters that can be used as gas oil substitutes, comprises: stage (a) oil, fat or a glyceride mixture is transesterified by ethanol using a soluble catalyst or a catalyst that becomes soluble during the reaction; stage (b) resultant glycerin is decanted and removed, without requiring an excess ethanol evaporation operation, stage (c) a second transesterification is conducted to obtain a product whose ester content is at least 97% by mass, stage (d) evaporation of excess ethanol is carried out in the presence of the catalyst under suitable conditions preventing a reverse transesterification reaction, the resultant ethanol being practically anhydrous, stage (e) the ester undergoes purification by water wash sequences, and stage (f) the ester is dried under reduced pressure.

21 Claims, 1 Drawing Sheet

METHOD FOR MANUFACTURING ETHYL ESTERS FROM FATTY SUBSTANCES OF NATURAL ORIGIN

This application relates to concurrently filed US application "Refined Method for Manufacturing Ethyl Esters from Fatty Substances of Natural Origin," having eattorney docket number PET-2275, invented by Mr. Gerard Hillion and Mr. Bruno Felfort, and relating to French application 05/09.733 filed on Sep. 21, 2005.

The present invention relates to the manufacture of fatty acid ethyl esters that can be used as gas oil substitutes, from natural fat or oils, vegetable or animal, or from other glyceride mixtures.

The object thereof is more particularly an improved transesterification method allowing, from natural fat or oils, vegetable or animal, or from other glyceride mixtures, to obtain in a quasi-quantitative way fatty acid ethyl esters.

BACKGROUND OF THE INVENTION

The transesterification reaction using methanol and ethanol is well known to the man skilled in the art. It most commonly uses homogeneous catalysts, for example acid catalysts (sulfonic acids, sulfuric acid, etc.), as described notably in patent U.S. Pat. No. 4,695,411, various metallic compounds, for example metallic salts such as titanium, zinc, magnesium, tin, antimony or lead salts, and these metallic compounds can be used in form of alcoholates, alkyl derivatives or oxides. Preferably, owing to the high reactivity thereof, homogeneous basic catalysts of NaOH, KOH or LiOH type in solution in methanol are more particularly used, or directly alcoholates of these metals, or even certain carbonates such as potassium carbonate and sodium carbonate for example, as mentioned by Freedman B. Et al.: JAOCS 61 No. 10, p. 1638; by Pryde E. H., "Vegetable Oil Fuels", Proc. Int. Conf., Fargo, N.D., 1982, pp. 117-122; and in patent U.S. Pat. No. 2,383,602.

Transesterification in the presence of methanol is generally carried out in a single catalysis stage in the case of a batch reaction or at least in two catalysis stages in the case of a continuous operation using overflow reactors as described in patent U.S. Pat. No. 5,354,878.

The ethanolysis methods described are few and much less effective than those using methanol. In fact, with ethanol and with the same alcohol/oil molar ratio than with methanol, it is impossible to obtain naturally separation of the glycerol formed (see notably patent U.S. Pat. No. 2,383,602).

The solvent power of ethanol being much higher than that of methanol, the consequence is that the glycerin formed during the reaction is made soluble. The conversion to esters is penalized thereby, which does not allow a high conversion in a single reaction stage to be obtained.

A second transesterification stage is thus necessary after removing the glycerin formed from the reaction medium.

Partial ethanol distillation or addition of a certain amount of water or of a third solvent such as a hydrocarbon, n-heptane for example, allows the solubility of the glycerin to be decreased and a sufficient amount thereof to be eliminated, which allows to reach a high conversion in the second catalysis stage. Another option allowing high conversions to be obtained consists in distilling under certain conditions and under reduced pressure the ethyl esters produced during the first transesterification stage.

SUMMARY OF THE INVENTION

Surprisingly, it has now been discovered that it is possible to carry out ethanolysis of an oil, a fat, or any other glyceride mixture, in two catalysis stages using a soluble basic catalyst, while obtaining natural decantation of the glycerin after the first transesterification stage without requiring excess alcohol distillation or addition of water or of a third solvent.

DETAILED DESCRIPTION OF THE INVENTION

Figure 1:
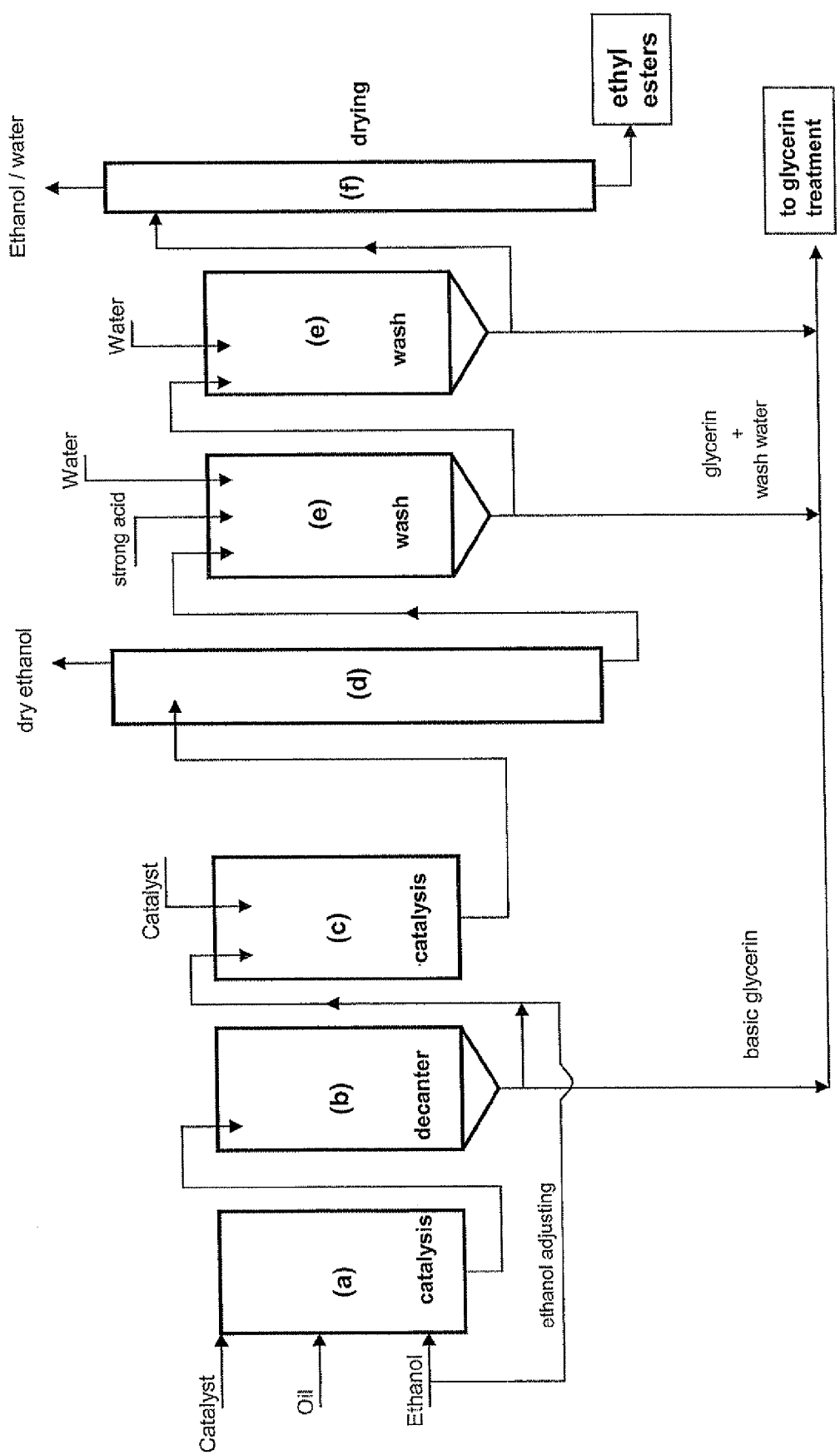
FIG. 1 shows a block-diagram with the various stages of the ethanolysis of a vegetal oil.

The invention thus provides a method for manufacturing fatty acid ethyl esters from vegetable or animal oils or fat or from other glyceride mixtures, wherein the transesterification stages are carried out in batch mode (discontinuous), and comprising the succession of stages as follows:

a stage (a) wherein the oil, the fat or the glyceride mixture is transesterified by ethanol using a soluble catalyst or a catalyst that becomes soluble during the reaction, a stage (b) wherein the glycerin formed is decanted and removed (without requiring an excess ethanol evaporation operation), a stage (c) wherein a second transesterification reaction is earned out so as to obtain a product whose ester content is at least 97% by mass, a stage (d) wherein evaporation of the excess ethanol is carried out in the presence of the catalyst under suitable conditions preventing a reverse transesterification reaction (or retroreaction), the ethanol obtained being then practically anhydrous, a stage (e) wherein the ester undergoes purification by means of water wash sequences, and a stage (f) wherein the ester mixture is dried under reduced pressure.

In the method according to the invention, a conversion to manufactured esters greater than or equal to 90% is readily obtained at the end of the first catalysis stage [stage (a)] by judiciously distributing the ethanol stoichiometry over the two transesterification stages (a) and (c) and by using as the catalyst either an alkaline alcoholate obtained by dissolution in an alcohol (methanol or ethanol) of a sodium, potassium or lithium hydroxide, or a commercially available methanolic sodium methylate solution. It is then possible, after removing the glycerin formed, to carry out the second catalysis stage [stage (c)] after adding makeup ethanol and catalyst. The conversion to ethyl esters thus obtained is then sufficient to reach the required quality for a mixture of esters intended for use as fuel.

Using as the catalyst in stages (a) and (c) an alkaline metal alcoholate, sodium or potassium ethylate or methylate for example, advantageously allows to obtain practically anhydrous ethanol at the end of the second catalysis stage. In fact, the alcoholate acts as a desiccant, as shown by the chemical hydrolysis equation of the alcoholate by water (the water coming essentially from the feedstocks: oil and ethanol). This reaction is stoichiometric and, in the case of methylate, it is written as follows:

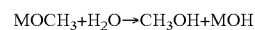

(where M represents the alkaline metal). This is a neat way of physically removing the water from the reaction medium.

The excess ethanol present in the reaction medium that is evaporated after the second catalysis stage [stage (c)] is practically anhydrous and has the advantage of being recycled without requiring a rectification stage. This evaporation is carried out under conditions preventing a retroreaction that consists in the reaction of glycerin with the manufactured ethyl esters so as to form glycerides and ethanol again. The temperature and the residence time are the two main parameters that influence the velocity of this reverse reaction.

The various stages of the method according to the invention are described more in detail hereafter in connection with the appended figure.

Stage (a)

The initial oil, fat, vegetable or animal, or the initial mixture of glycerides generally has an acid number of at most 2. Ethanol whose water content ranges for example between 3000 and 5000 ppm is generally used, using an ethanol/oil stoichiometry such as to obtain a conversion to manufactured esters greater than or equal to 90%. This ethanol/oil stoichiometry generally ranges between 1.3 and 2, preferably between 1.6 and 1.8.

The advantage of this stage in the method according to the invention is that the implementation thereof allows, in next stage (b), natural decantation of the glycerin without requiring any excess ethanol evaporation operation.

The catalyst used is a homogeneous basic catalyst, i.e. a soluble catalyst, or a catalyst that becomes soluble during the reaction. It can be obtained for example by dissolution of a strong base in an alcohol (methanol or ethanol), or from an alkaline metal alcoholate, which can be for example a sodium ethylate or methylate, or from a metallic compound of alcoholate, alkyl and/or oxide type. Sodium methylate is preferably used because it has the advantage of being cheap, industrially available in 30% solution in methanol.

The reaction temperature generally ranges between 20° C. and 100° C., preferably between 40° C. and 80° C.

In batch mode, the reaction time allowing thermodynamic equilibrium to be reached generally ranges between 40 and 160 minutes.

It can be noted that, if an alkaline metal methylate in solution in methanol is used as the catalyst, the mixture of esters obtained will contain a certain proportion of methyl esters, generally ranging between 10 and 15% by mass.

Stage (b)

Natural decantation of the glycerin is obtained as soon as stirring stops and at a medium temperature ranging for example between 40° C. and 60° C. The glycerin contained in the lower phase is then eliminated by draw-off Stage (c)

This second transesterification stage is carried out after adding a new amount of alkaline catalyst and an amount of ethanol corresponding to an initial ethanol/oil stoichiometry generally ranging between 0.3 and 1, preferably between 0.5 and 0.7.

The catalysis temperature is of the same order as that of stage (a), with a catalysis time ranging between 20 and 45 minutes.

This stage (c) allows to obtain a product whose ester content is at least 97% by mass.

Stage (d)

In this stage, removal of the excess ethanol from the reaction medium is generally carried out by evaporation in the presence of the catalyst. The ethanol obtained is practically anhydrous and it can be recycled in the process without requiring rectification.

The evaporation conditions have to be adapted so as to prevent retroreaction, which consists in that the glycerol formed reacts with the manufactured ethyl esters by forming partial (mono and diglycerides) or total (triglycerides) glycerides again, thus restoring the initial oil.

The residence time and the temperature are the two main parameters that influence the velocity of this reverse reaction. Using a falling film type evaporator is in this case preferred to reduce the residence time. The temperature is generally below 120° C., preferably below 100° C. The residence time is generally below 1 minute, preferably below 30 seconds.

Stage (e)

In this stage, the ester phase is purified by being freed from the residual catalyst and from the soluble glycerin by a succession of water wash operations.

If necessary, a first neutralizing wash that efficiently eliminates the traces of sodium soap contained in the ester phase can be carried out using a strong mineral acid such as sulfuric acid, hydrochloric acid or phosphoric acid, then one or more wash cycles are carried out with pure water depending on the strong excess acid elimination efficiency.

Stage (f)

Water and ethanol traces are eliminated by drying (evaporation under reduced pressure) so that the ester mixture meets the specifications required for a biodiesel fuel concerning the two criteria (water and ethanol content) of the EN 14214 standard.

NB: Reminder of the specifications from the EN 14214 standard:

Triglycerides=<0.2

Diglycerides=<0.20

Monoglycerides=<0.80

Fatty acid esters=96.50 mini

The following examples illustrate the method according to the invention.

EXAMPLE 1 (COMPARATIVE)

Ethanolysis Reaction 500 g refined colza oil of alimentary quality and 180 g ethanol containing at most 1000 ppm water, which corresponds to an alcohol/oil stoichiometry of 2.3, is fed into a stirred double-walled glass reactor equipped with a bottom valve and heated to 70° C. 8 g of a 30% methanolic sodium methylate solution is added as soon as a temperature of 70° C. is reached. Stirring and the 70° C.±2° C. temperature are maintained for 60 minutes.

Samples are taken after 20, 30, 45 and 60 minutes. On each sample, the active catalyst is immediately destroyed through the action of a 10% aqueous sulfuric acid solution, which freezes the conversion. The supernatent ester phase is then analyzed.

Liquid gel-permeation chromatography allows to determine the composition of the mixture of esters and of partial glycerides.

There is no more conversion evolution between 45 and 60 minutes of catalysis time, which means that thermodynamic equilibrium of the transesterification reaction is reached after a 45-minute residence time.

The composition, expressed in % by mass, is as follows:

Triglycerides=0.03

Diglycerides=0.4

Sterols and derivatives=1.6

Monoglycerides=3.02

Fatty acid esters=94.95.

EXAMPLE 2 (COMPARATIVE)

Methanolysis Reaction 500 g refined colza oil of alimentary quality and 125 g methanol containing at most 1000 ppm water, which corresponds to an alcohol/oil stoichiometry of 2.3, is fed into a stirred double-walled glass reactor equipped with a bottom valve. 8 g of a 30% methanolic sodium methylate solution is added as soon as a temperature of 70° C. is reached. Stirring and the 70° C.±2° C. temperature are maintained for 60 minutes.

Samples are taken after 20, 30, 45 and 60 minutes. On each sample, the active catalyst is immediately destroyed through the action of a 10% aqueous sulfuric acid solution, which freezes the conversion. The supernatent ester phase is then analyzed.

Liquid gel-permeation chromatography allows to determine the composition of the mixture of esters and of partial glycerides.

There is no more conversion evolution between 45 and 60 minutes of catalysis time, which means that thermodynamic equilibrium of the transesterification reaction is reached after a 45-minute residence time.

The composition, expressed in % by mass, is as follows:
Triglycerides=0.05
Diglycerides=0.10
Sterols and derivatives=1.6
Monoglycerides=0.75
Fatty acid esters=97.50.

EXAMPLE 3 (According to the Invention)

1000 g refined colza oil of alimentary quality and 266 g ethanol containing 3000 ppm water, respecting an alcohol/oil stoichiometry of 1.7, is fed into a stirred glass reactor equipped with a bottom valve and heated to 70° C. 10 g of a 30% methanolic sodium methylate solution is then added. Stirring and the 70° C.±2° C. temperature are maintained for 60 minutes (stage (a)).

In stage (b), the reaction medium is decanted at 60° C. 15 to 20 minutes after stirring is stopped, 95 g of a glycerin solution consisting of glycerin, ethanol, ethyl esters, sodium soaps and sodium alcoholates (mixture of methylate, ethylate and glycerate) is drawn off.

After this first transesterification reaction, the composition of the mixture is as follows (in % by mass):
ethyl and methyl esters: 91.5
triglycerides: 0.9
diglycerides: 2.6
monoglycerides: 3.7
sterols and sterol esters: 1.3.

A second transesterification stage is carried out in stage (c). 93 g ethanol containing approximately 3000 ppm water, which corresponds to an initial ethanol/oil stoichiometry of 0.6, and 3.33 g sodium methylate in 30% solution in methanol is added to the ester phase. The medium is stirred at 60° C. for at least 30 minutes.

Under such temperature conditions, the glycerin formed remains soluble in the reaction medium.

At the end of this second transesterification reaction, the composition of the mixture is as follows (in % by mass):
ethyl and methyl esters: 97.5
triglycerides: <0.1
diglycerides: 0.2
monoglycerides: 0.7
sterols and sterol esters: 1.6.

In stage (d), the major part of the excess ethanol is removed from the reaction medium by continuous supply of a falling film evaporator.

The operating conditions are as follows:
rate of supply: 600 ml/hour,
falling film set-point temperature: 100° C.,
pressure: 160 mm Hg,
mean residence time estimated between 15 and 20 seconds.

Under such conditions, no retroreaction is observed. Starting from an initial ethanol content of approximately 17% in the ester mixture, a residual ethanol content ranging between 1.8 and 2% by mass is obtained at the end of this stage. The water content of the distilled ethanol is below 400 ppm.

In stage (e), the ethyl ester phase obtained is purified by carrying out a water wash sequence.

All of the reaction mixture is fed into the reactor equipped with a bottom valve and the temperature is brought to 60° C. 30 g deionized water is added, then the mixture is stirred for 5 minutes and decanted for 15 to 20 minutes. An aqueous phase rich in alcohol, glycerin and sodium salts is collected. This operation is repeated until the pH value obtained for the aqueous solution ranges between 7 and 8.

The composition of the mixture of esters obtained, which respects the EN 14214 standard relative to biodiesel fuels, is as follows (in % mass):
ethyl and methyl esters: 97.5
triglycerides: <0.1
diglycerides: 0.2
monoglycerides: 0.7
sterols and sterol esters: 1.6

1023 g of a mixture of ethyl and methyl esters containing 10.3% methyl esters is eventually collected. The presence of methyl esters is due to the use of sodium methylate as the catalyst, all of the methanol used being then converted to methyl esters.

EXAMPLE 4 (COMPARATIVE)

Example 3 is repeated identically except that, in stage (d), the set-point temperature of the falling film is brought to 148° C.

The residual amount of ethanol in the ester mixture is below 0.3%.

Under such conditions, a retroreaction is observed, as shown by the composition of the mixture obtained (in % by mass):
ethyl and methyl esters: 66.2
triglycerides: 13.9
diglycerides: 16.1
monoglycerides: 2.2
sterols and sterol esters: 1.6

EXAMPLE 5 (COMPARATIVE)

Example 3 is repeated identically, up to and including stage (e).

Stage (d), which consists in eliminating the major part of the excess ethanol, is carried out in batch mode in the reactor equipped with a bottom valve.

The operating conditions are: a reaction medium temperature of 100° C. and a pressure of 160 mm Hg.

The evaporation time required to reach a residual ethanol content of the order of 1.5% by mass is 30 minutes.

Under such conditions, the retroreaction is effective as shown by the composition of the mixture (in % by mass):
ethyl and methyl esters: 94.4
triglycerides: 0.4 diglycerides: 1.9
monoglycerides: 1.7
sterols and sterol esters: 1.6.

The results of this example show that, despite a temperature of 100° C., similar to the temperature used in example 1, the residence time is an important parameter that conditions the appearance of a retroreaction. The falling film appears to be the preferred tool for combining a suitable temperature and residence time.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 05/09.734, filed Sep. 21, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for catalytically manufacturing fatty acid ethyl esters from vegetable or animal oils or fat or from other glyceride mixtures, consisting essentially of a succession of stages as follows:
   a stage (a) wherein the oil, the fat or the glyceride mixture is transesterified by an alcohol in the presence of a catalyst, wherein said alcohol consists essentially of ethanol and optionally a quantity of methanol derived from said catalyst, said catalyst being a soluble catalyst or a catalyst that becomes soluble during the reaction, thereby forming a mixture of esters and glycerine,
   a stage (b) wherein the glycerin formed is decanted from said mixture of esters and glycerine and removed to obtain an ester product,
   a stage (c) wherein a second transesterification reaction is carried out on the ester product from stage (b) with ethanol in the presence of a catalyst so as to obtain an ester product whose ester contents is at least 97% by mass,
   a stage (d) wherein the ester product from stage (c) is subjected to evaporation of excess ethanol said evaporation being carried out in the presence of a catalyst in a falling film type evaporator at a temperature below 120° C. and with a residence time below 1 minute thereby preventing a reverse transesterification reaction, the ethanol obtained being then practically anhydrous,
   a stage (e) wherein the ester product from stage (d) undergoes purification by means of water wash sequences, and
   a stage (f) wherein the ester product from stage (e) is dried under reduced pressure.

2. A method as claimed in claim 1, comprising conducting stage (a), with a vegetable or animal oil or fat or a glyceride mixture whose acid number is at most 2 and ethanol having water content between 3000 and 5000 ppm, and an ethanol/oil stoichiometric ratio ranging between 1.3 and 2.

3. A method as claimed in claim 2, wherein said ethanol/oil stoichiometric ratio ranges between 1.6 and 1.8.

4. A method as claimed in claim 1, comprising conducting stages (a) and (c), with catalyst obtained by dissolution of a strong base in alcohol, or from an alkaline metal alcoholate, or from a metallic compound of alcoholate, alkyl and/or oxide.

5. A method as claimed in claim 4, wherein sodium methylate in solution in methanol is the catalyst.

6. A method as claimed in claim 1, comprising conducting stages (a) and (c), at a reaction temperature between 20° C. and 100° C.

7. A method as claimed in claim 1, comprising conducting stage (a), in a batch mode for a sufficient time for the reaction to reach thermodynamic equilibrium at between 40 and 160 minutes.

8. A method as claimed in claim 1, comprising conducting stage (b), decantation of the glycerin at a temperature ranging between 40° C. and 60° C.

9. A method as claimed in claim 1, comprising conducting stage (c), with the amount of ethanol corresponding to an initial ethanol/oil stoichiometric ratio of between 0.3 and 1.

10. A method as claimed in claim 9, wherein said initial ethanol/oil stoichiometric ratio ranges between 0.5 and 0.7.

11. A method as claimed in claim 9, comprising conducting stage (c), for between 20 and 45 minutes with a catalyst.

12. A method as claimed in claim 1, comprising conducting stage (e), with first neutralizing wash a strong mineral acid, followed by one or more wash cycles with pure water.

13. A method as claimed in claim 2, comprising conducting stage (d), in a falling film type evaporator at a temperature below 120° C. and with a residence time below 30 seconds.

14. A method as claimed in claim 6, comprising conducting stage (d), in a falling film type evaporator at a temperature below 120° C. and with a residence time below 30 seconds.

15. A method as claimed in claim 7, comprising conducting stage (d), in a falling film type evaporator at a temperature below 120° C. and with a residence time below 30 seconds.

16. A method as claimed in claim 8, comprising conducting stage (d), in a falling film type evaporator at a temperature below 120° C. and with a residence time below 30 seconds.

17. A method as claimed in claim 10, comprising conducting stage (d), in a falling film type evaporator at a temperature below 120° C. and with a residence time below 30 seconds.

18. A method as claimed in claim 10, comprising conducting stage (c), for between 20 and 45 minutes with a catalyst.

19. A method as claimed in claim 18, comprising conducting stage (a), with a vegetable or animal oil or fat or a glyceride mixture whose acid number is at most 2 and ethanol having water content between 3000 and 5000 ppm, and an ethanol/oil stoichiometric ratio ranging between 1.3 and 2.

20. A method as claimed in claim 1, comprising conducting stage (d), in a falling film type evaporator at a temperature below 120° C. and with a residence time below 30 seconds.

21. A method for catalytically manufacturing fatty acid ethyl esters from vegetable or animal oils or fat or from other glyceride mixtures, consisting of a succession of stages as follows:
   a stage (a) wherein the oil, the fat or the glyceride mixture is transesterified by an alcohol in the presence of a catalyst, wherein said alcohol consists essentially of ethanol and optionally a quantity of methanol derived from said catalyst, said catalyst being a soluble catalyst or a catalyst that becomes soluble during the reaction, thereby forming a mixture of esters and glycerine, a stage (b) wherein the glycerin formed is decanted from said mixture of esters and glycerine and removed to obtain an ester product, a stage (c) wherein a second transesterification reaction is carried out on the ester product from stage (b) with ethanol in the presence of a catalyst so as to obtain an ester product whose ester content is at least 97% by mass, a stage (d) wherein the ester product from stage (c) is subjected to evaporation of excess ethanol said evaportation being carried out in the presence of a catalyst in a falling film type evaporator at a temperature below 120° C. and with a residence time below 1 minute thereby preventing a reverse transesterification reaction, the ethanol obtained being then practically anhydrous, a stage (e) wherein the ester product from stage (d) undergoes purification by means of water wash sequences, and a stage (f) wherein the ester product from stage (e) is dried under reduced pressure.

* * * * *

UNITED STATES PATENT AND TRADEMARK OFFICE
CERTIFICATE OF CORRECTION

PATENT NO. : 7,566,794 B2  Page 1 of 1
APPLICATION NO. : 11/523735
DATED : July 28, 2009
INVENTOR(S) : Hillion et al.

It is certified that error appears in the above-identified patent and that said Letters Patent is hereby corrected as shown below:

Column 8, line 30, reads "stage (e), with first neutralizing wash a strong mineral acid,", should read -- stage (e), with a first neutralizing wash with a strong mineral acid, --.

Signed and Sealed this

Seventeenth Day of November, 2009

David J. Kappos
*Director of the United States Patent and Trademark Office*